(12) United States Patent
Sheiman

(10) Patent No.: US 8,671,935 B2
(45) Date of Patent: Mar. 18, 2014

(54) SYNERGISTIC DRUG DELIVERY DEVICE

(75) Inventor: Vladimir Sheiman, Sydney (AU)

(73) Assignee: Sheiman Ultrasonic Research Foundation PTY Ltd., Sydney, New South Wales (AU)

(*) Notice: Subject to any disclaimer, the term of this patent is extended or adjusted under 35 U.S.C. 154(b) by 67 days.

(21) Appl. No.: 13/210,650

(22) Filed: Aug. 16, 2011

(65) Prior Publication Data

US 2012/0095279 A1   Apr. 19, 2012

Related U.S. Application Data

(62) Division of application No. 10/525,373, filed as application No. PCT/AU03/01079 on Aug. 23, 2003, now Pat. No. 8,001,962.

(30) Foreign Application Priority Data

Aug. 23, 2002 (AU) .............................. 2002950965
Dec. 2, 2002 (AU) .............................. 2002953039

(51) Int. Cl.
    *A61M 11/00*   (2006.01)

(52) U.S. Cl.
    USPC ............ 128/200.24; 128/200.14; 128/200.16; 128/200.18; 239/338; 239/370; 239/102.1; 239/102.2

(58) Field of Classification Search
    USPC ............ 128/200.14, 200.16, 200.18, 200.24; 239/338, 370, 102.1, 102.2, DIG. 11
    See application file for complete search history.

(56) References Cited

U.S. PATENT DOCUMENTS

| | | | |
|---|---|---|---|
| 5,483,953 A * | 1/1996 | Cooper .................... | 128/200.22 |
| 5,511,726 A * | 4/1996 | Greenspan et al. ........ | 239/102.2 |
| 6,533,803 B2 * | 3/2003 | Babaev ......................... | 607/89 |
| 6,629,974 B2 * | 10/2003 | Penny et al. .................... | 606/41 |
| 6,915,962 B2 * | 7/2005 | Power et al. ............... | 239/102.2 |
| 7,891,580 B2 * | 2/2011 | Valpey et al. .............. | 239/102.2 |
| 2007/0119969 A1 * | 5/2007 | Collins et al. ............. | 239/102.1 |

* cited by examiner

*Primary Examiner* — Steven Douglas
(74) *Attorney, Agent, or Firm* — Miles & Stockbridge P.C.

(57) ABSTRACT

The invention relates generally to a device for delivering a substance in an aerosol, liquid or cream form into a cellular organism with the assistance of asymmetric pulse magnetic energy and ultrasound.

10 Claims, 2 Drawing Sheets

SYNERGISTIC DRUG DELIVERY DEVICE

CROSS-REFERENCE TO RELATED APPLICATION

This application is a division of application Ser. No. 10/525,373 filed Jan. 17, 2006 now U.S. Pat. No. 8,001,962, which is a 371 of International Application No. PCT/AU2003/001079 filed Aug. 23, 2003.

FIELD OF THE INVENTION

The present invention relates to a device for delivering a substance in an aerosol form into a cellular organism.

BACKGROUND OF THE INVENTION

Transdermal drug delivery can involve passive diffusion and active transport. Passive diffusion of a drug through the skin is the diffusion that occurs naturally when small-molecule drugs are applied to the skin in sufficient concentration and for a sufficient period of time to enable natural diffusion through the skin. However, passive diffusion is slow and furthermore, because of the skin's natural barriers to passage of externally applied substances, passive diffusion is not suitable for most drugs. Active transdermal drug delivery techniques include sonophoresis, iontophoresis, electroporation and magnetophoresis. Sonophoresis involves the application of ultrasound, iontophoresis and electroporation involve the application of an electric field and magnetophoresis involves the application of a magnetic field.

U.S. Pat. No. 5,741,317 discloses an apparatus which includes a therapy and drug treatment tub for submersion of a treatment area of a patient in a medicated solution. The tub includes acoustic transducers and rows of electrodes and coils for delivery of respective ultrasonic, electric and magnetic radiation to the patient. The radiation facilitates active transdermal drug delivery involving phonophoretic, iontophoretic and electromagnetophoretic transport mechanisms. However, the apparatus is very large and expensive and cannot readily be used for transdermal drug delivery to a specific region of a patient.

U.S. Pat. No. 5,983,134 discloses a flexible cuff connected to a liquid drug reservoir. The cuff is designed for attachment to a patient by wrapping around part of the patient's body to form an attached sleeve. Referring to FIG. 1 of U.S. Pat. No. 5,983,134, the attached sleeve can be elongate and encircle most of a patient's leg, or squat and encircles a patient's neck. The cuff is designed to transmit electric and magnetic fields to assist transdermal delivery of drugs provided at an internal cylindrical surface of the attached sleeve. While the cuff of U.S. Pat. No. 5,983,134 is suitable for transdermal drug delivery to a specific part of a patient's body, it is cumbersome to use and is only suitable for delivery of a drug to a circumferential segment of a patient's limb, torso or neck.

U.S. Pat. No. 5,464,386 discloses a transdermal drug delivery applicator which is designed to supply a fluid medium carrying drug loaded vesicles to a patient's skin via a curved head assembly. The applicator generates a pulsed electrical field to facilitate active transdermal transport mechanisms of electroporation and iontophoresis. The applicator is capable of providing active transdermal drug delivery to a specific part of a patient's body. However, the applicator is only able to provide active transdermal drug delivery involving electric radiation.

SUMMARY OF THE INVENTION

In a first aspect, the present invention provides a device for delivering a substance into a cellular organism, the device comprising:

an aerosol delivery head for providing the substance in an ionised aerosol form at a delivery region of the organism; and means for generating radiation or magnetic energy which is applied to the delivery region to enhance delivery of the ionised aerosol to the organism.

In a preferred embodiment, the aerosol delivery head comprises an aerosol delivery compartment. The aerosol delivery compartment is preferably arranged to substantially evenly distribute aerosol over the delivery region. The aerosol delivery compartment may have an inlet for receipt of aerosol. The inlet may be arranged for receipt of aerosol from a nebulizing device for direct supply of aerosol therefrom. The inlet may be sealable.

The compartment may comprise an outlet arranged for application of the substance to the delivery region.

Suitably, the radiation or magnetic energy generating means of the present invention generates radiation fields in the form of magnetic or ultrasonic radiation fields.

The radiation or energy generating means of the present invention may be arranged for simultaneous generation of two different forms of radiation or energy. The radiation or energy generating means of the present invention are preferably arranged to simultaneously generate different forms of radiation or energy so that they combine synergistically to enhance delivery of the substance.

The radiation or energy generating means of the present invention preferably comprises one or more radiation field generators, including a magnetic field generator and an ultrasonic field generator.

The delivery head may comprise a substance delivery component. The substance delivery component is preferably arranged to substantially evenly distribute the substance over the delivery region. The substance delivery component may comprise a substance delivery plate. Alternatively, the substance delivery component may comprise a substance delivery compartment. The substance delivery compartment may have an inlet for receipt of the substance. The substance delivery compartment may have an outlet for application of the substance to the delivery region. The inlet and outlet may be the same.

The substance delivery device of the present invention may further comprise ionisation means for respective ionisation of the aerosol or substance and provision of their ionised forms at the delivery region.

The organism of the present invention may be an animal. More particularly, the organism may be a human being. The delivery region of the present invention may comprise a membrane of the animal or human being. The membrane may comprise skin of the human being. Alternatively, the membrane may comprise a cornea of the human being.

BRIEF DESCRIPTION OF THE DRAWINGS

A preferred embodiment of the present invention will now be described, by way of example only, with reference to the accompanying drawings, in which.

DETAILED DESCRIPTION OF THE PREFERRED EMBODIMENTS

Figure 1:
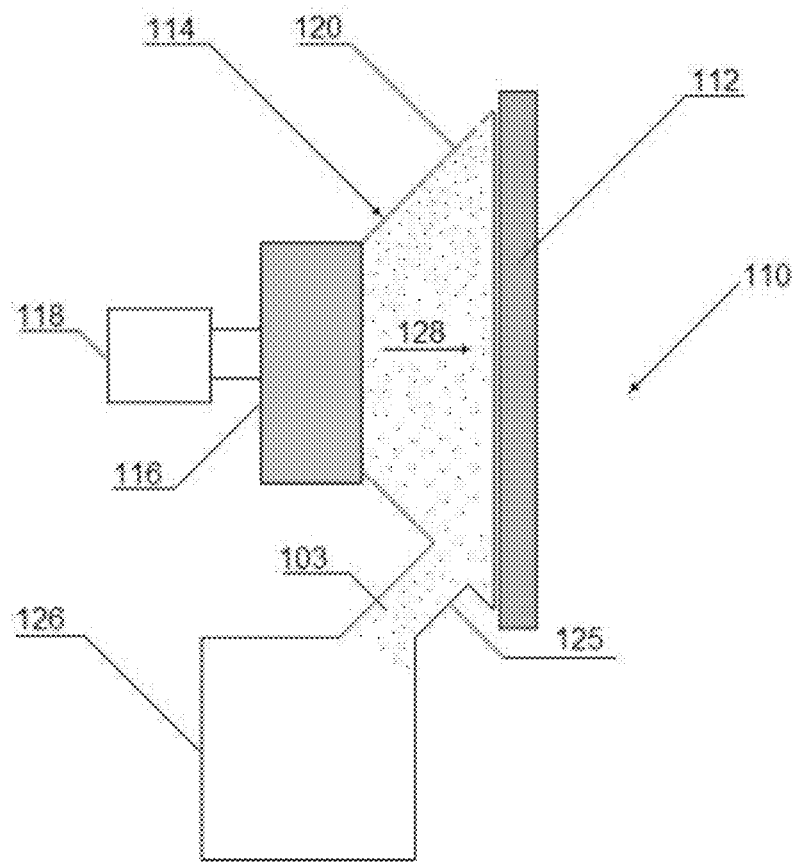
FIG. 1 is a schematic side elevational view of a magnetic radiation transdermal aerosol delivery gun.

Referring to FIG. 1, aerosol produced by an ultrasonic nebulizer is administered to a delivery region of a cellular organism in the form of a patient treatment site 112. This is effected by the use of a substance delivery device which in this example is also a handheld device in the form of an aerosol delivery gun 110.

In this example, the patient treatment site 112 is a specific region of the skin of a patient which requires administration of an aerosol form of a drug. However, the patient treatment site could be for example a patient's cornea. The aerosol delivery gun 110 includes radiation or energy generating means for enhancing delivery of aerosol 103 to the patient treatment site 112. In this particular example the radiation or energy generating means is a magnetic field generator which includes a magnetic inductor 116 and a corresponding electronic generator 118. The aerosol delivery gun 110 also includes an aerosol delivery head which in this example comprises aerosol delivery compartment 114 for provision of aerosol 103 to the patient treatment site 112.

The aerosol delivery compartment 114 includes walls 120 which extend away from the magnetic inductor 116 in a divergent manner. A compartment outlet in the form of an aerosol outlet is formed between ends of the delivery compartment walls 120 which are designed for application against the patient treatment site 112 to create a substantially sealed compartment. If the patient treatment site is a patient's cornea, the aerosol delivery compartment is designed so that the ends of its walls 120 contact skin covering the patient's eye socket to form a substantially sealed compartment covering the cornea. The substantially sealed compartment enables aerosol 103 to be contained between the patient treatment site 112 and the magnetic inductor 116, and evenly dispersed over the patient treatment site 112. The aerosol 103 can be supplied to the aerosol compartment 114 via a closed compartment, for example, closed compartment 126 or, alternatively, can be supplied directly from a nebulizer via an inlet in the form of inlet pipe 125.

With aerosol 103 contained within the aerosol delivery compartment 114 as shown in FIG. 1, passive transdermal aerosol delivery to the patient via the patient treatment site 112 is more effective than it would be if the aerosol was otherwise delivered. The aerosol delivery compartment 114 of the aerosol delivery gun 110 therefore enhances transdermal drug delivery by concentrating aerosol 103 near the patient treatment site 112 and evenly distributing it over that site.

The aerosol delivery gun 110 further enhances transdermal delivery of aerosol 103 which condenses on the patient treatment site 112 by applying a magnetic field, via the magnetic inductor 116, to the patient treatment site 112. The general direction of propagation of the magnetic field is represented by arrow 128.

The aerosol delivery gun 110 is effective for delivery of a substance to sensitive patient treatment areas, for example, a patient's cornea. It enables the substance to be applied to the cornea without the cornea being contacted by anything other than the aerosol 103. This is possible because the magnetic field generator of the aerosol delivery gun 110 does not contact the patient treatment site.

By ionising the aerosol 103 it can be more efficiently and effectively delivered to the patient treatment site 112. The ionised aerosol 103 is attracted to the patient treatment site 112 by oppositely charging the patient treatment site 112. The aerosol 103 can be charged before or after its entry into the aerosol delivery compartment 114.

Figure 2:
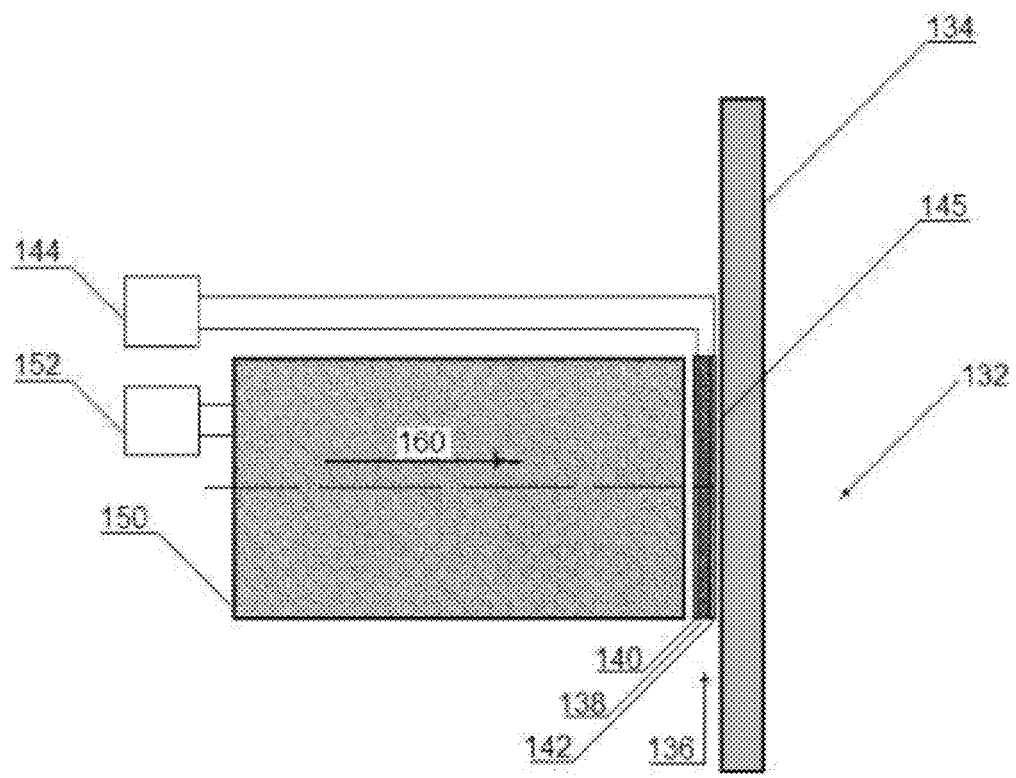
FIG. 2 is a schematic side elevational view of one example of internal components of a substance delivery gun similar to the aerosol delivery gun of FIG. 1.

FIG. 2 schematically depicts another example of a handheld device in the form of a substance delivery gun 132 which is suitable for delivering a substance, for example, in aerosol, liquid or gel form, to a delivery region of a cellular organism which in this example is patient treatment site 134. The patient treatment site 134 is identical to the patient treatment site 112 described above in relation to the aerosol delivery gun 110.

The substance delivery gun 132 houses means for generation of sonic or ultrasonic and magnetic radiation. The substance delivery gun 132 also includes a radiation delivery head which can take the form of a radiation delivery plate 141 (see FIG. 2).

The substance delivery gun 132 further enhances transdermal substance delivery by simultaneously applying ultrasonic and magnetic fields to the patient treatment site 134 when, in the case of the substance delivery plate 145, a gel form of a substance is located at the patient treatment site 134. The ultrasonic and magnetic radiation applies to the substance respective active transdermal transport techniques of sonophoresis and magnetophoresis.

Referring to FIG. 2, the substance delivery gun 132 includes an ultrasonic field generator which in this example consists of an electro acoustic transducer 136 and an electronic generator 144. The electronic generator 144 supplies power to the electro acoustic transducer 136. The electro acoustic transducer is formed of a piezoceramic 138 which is covered on opposite sides by metal electrodes 140 and 142. The electro acoustic transducer 136 is formed of diamagnetic material which is transparent to magnetic fields generated by the magnetic field generator.

The electro acoustic transducer 136 is designed to operate at two frequencies. At a low to mid frequency the transducer induces transdermal cavitation, a mechanism of sonophoresis. At a second significantly higher frequency the electro acoustic transducer 136 does not induce cavitation and is used in combination with the low to mid frequency ultrasonic radiation to avoid tissue damage which is known to occur with low to mid frequency ultrasonic radiation when it is applied at high power.

The magnetic field generator of the substance delivery gun 132 is in this particular example a magnetic inductor 150 which is supplied electric current by an electronic generator 152. The electronic generator 152 is designed to produce different forms of voltage to create different types of magnetic fields including asymmetric pulse magnetic fields.

The general direction of propagation of the ultrasonic, electric and magnetic fields is represented by arrow 160. The radiation field generators of the substance delivery gun 132 are designed to simultaneously generate each of the two forms of radiation fields. The fields are one example of how ultrasonic and magnetic fields can be combined in a synergistic manner whereby the two different forms of radiation fields collectively enhance delivery more than the sum of delivery enhancements achievable through independent application of the two different forms of radiation fields.

Now that various examples of a preferred embodiment and method of delivering a substance into a cellular organism have been described, it will be apparent to those skilled in the art that the preferred embodiment and methodology have at least the following advantages:

(a) the application of an aerosol form of a substance to delivery regions of a cellular organism is possible where contact of the delivery regions by liquid or solid matter is adverse or sensitive;

(b) the delivery of an aerosol form of a substance into a cellular organism is possible through active transport techniques involving the application of one or more forms of radiation or energy;

(c) the delivery of an aerosol form of a substance into a cellular organism is possible through simultaneous application of two or more different forms of radiation or energy;

(d) the delivery of an aerosol form of a substance into a cellular organism is possible through simultaneous application of two or more different forms of radiation or energy in a synergistic manner whereby different form of radiation or energy collectively enhance delivery more than the sum of delivery enhancements achievable through independent application of the different forms of radiation or energy;

(e) the substance delivery can be confined to a relatively small part of a cellular organism by simultaneous application of two or more different forms of radiation via a radiation delivery head of a substance delivery gun; and (f) the delivery of a substance via a delivery gun through simultaneous application of two or more different forms of radiation or energy in a synergistic manner whereby different forms of radiation or energy collectively enhance delivery more than the sum of delivery enhancements achievable through independent application of the different forms of radiation or energy.

Those skilled in the art will appreciate that the invention described herein is susceptible to variations and modifications other than those specifically described. For example, the specific shape and design of the nebulizer, and the aerosol and substance delivery guns, as well as the specific shape, design or configuration of components or assemblies that they comprise may vary provided they function as broadly defined.

All such variations and modifications are to be considered within the scope of the present invention the nature of which is to be determined from the foregoing description.

The claims defining the invention are as follows:

1. A device for delivery of a substance into a cellular organism, said device comprising:
   an aerosol delivery head for providing the substance in an ionised aerosol form at a delivery region of the organism; and
   means for applying asymmetric pulse magnetic energy to the delivery region to effect enhanced delivery of the ionised aerosol substance to the cellular organism.

2. A device as defined in claim 1, wherein the aerosol delivery head provides a compartment about the delivery region.

3. A device as defined in claim 1, also comprising a nebulizer operatively coupled to the aerosol delivery head.

4. A device as defined in claim 1, further comprising means for generating ultrasonic energy being adapted to cooperate within the delivery region with the asymmetric pulse magnetic energy means to enhance delivery of the substance to the cellular organism; said ultrasonic generating means being operatively coupled to the asymmetric pulse magnetic energy means whereby a synergistic effect is provided by the combination of said means.

5. A device as defined in claim 4, wherein the substance is in a liquid, gel or a cream form.

6. A device for delivery of a substance into a cellular organism, said device comprising:
   an aerosol delivery head for providing the substance in an ionised aerosol form at a delivery region of the organism; and
   a magnetic pulse generator configured to apply asymmetric pulse magnetic energy to the delivery region to effect enhanced delivery of the ionised aerosol substance to the cellular organism.

7. A device as defined in claim 6, wherein the aerosol delivery head provides a compartment about the delivery region.

8. A device as defined in claim 6, also comprising a nebulizer operatively coupled to the aerosol delivery head.

9. A device as defined in claim 6, further comprising a source of ultrasonic energy configured to cooperate within the delivery region with the magnetic pulse generator to enhance delivery of the substance to the cellular organism; said source of ultrasonic energy being operatively coupled to the magnetic pulse generator whereby a synergistic effect is provided by the combination of the source of ultrasonic energy with the magnetic pulse generator.

10. A device as defined in claim 9, wherein the substance is in a liquid, gel or cream form.

* * * * *